United States Patent [19]
Butler

[11] Patent Number: 5,621,166
[45] Date of Patent: Apr. 15, 1997

[54] EXHAUST EMISSIONS ANALYSIS APPARATUS AND METHOD

[75] Inventor: James W. Butler, Livonia, Mich.

[73] Assignee: Ford Motor Company, Dearborn, Mich.

[21] Appl. No.: 417,523

[22] Filed: Apr. 6, 1995

[51] Int. Cl.$^6$ .................................................. G01M 15/00
[52] U.S. Cl. ................... 73/116; 250/338.5; 250/339.13; 250/343
[58] Field of Search .................................. 73/116, 23.31, 73/23.32; 250/338.5, 339.08, 339.13, 343, 345, 339.1; 356/51, 229, 438

[56] References Cited

U.S. PATENT DOCUMENTS

| | | | |
|---|---|---|---|
| 3,406,562 | 10/1968 | Perna, Jr. et al. | |
| 3,630,072 | 12/1971 | Traver. | |
| 3,973,848 | 8/1976 | Jowett et al. | |
| 4,160,373 | 7/1979 | Fastaia et al. | |
| 4,590,374 | 5/1986 | Brewster | 250/343 |
| 4,687,934 | 8/1987 | Passaro et al. | 250/343 |
| 4,924,095 | 5/1990 | Swanson, Jr. | |
| 4,950,900 | 8/1990 | Takeuchi et al. | 250/343 |
| 5,138,163 | 8/1992 | Butler et al. | 250/343 |
| 5,210,702 | 5/1993 | Bishop et al. | 250/338.5 |
| 5,245,406 | 9/1993 | Masutani | 250/339.08 |
| 5,251,008 | 10/1993 | Masutani | 250/339.08 |
| 5,268,745 | 12/1993 | Goody | 250/343 |
| 5,319,199 | 6/1994 | Stedman et al. | |
| 5,343,043 | 8/1994 | Johnson. | |
| 5,401,967 | 3/1995 | Stedman et al. | 250/338.5 |
| 5,416,325 | 5/1995 | Buontempo et al. | 250/339.08 |
| 5,418,366 | 5/1995 | Rubin et al. | 250/339.13 |

*Primary Examiner*—Richard Chilcot
*Assistant Examiner*—Eric S. McCall
*Attorney, Agent, or Firm*—Lorraine S. Melotik; Roger L. May

[57] ABSTRACT

Apparatus and method are provided for testing of exhaust gas emissions from an internal combustion engine, and determining the engine's operating condition. An inferred value for the ratio of hydrogen to carbon in the exhaust, based on measured values for the $H_2O$, $CO_2$ and CO components of the exhaust gas, is used to determine whether the engine and associated exhaust componentry have reached normal operating conditions. The emissions testing apparatus and method are suitable for remote testing of exhaust gas emissions from an internal combustion engine of an on-road motor vehicle. A light source emits preferably near to mid-infrared light to impinge upon the exhaust gas emissions. The emitted light includes wavelengths absorbed by exhaust species to be measured, including at least $H_2O$, $CO_2$ and CO. Following impingement on the exhaust gas emissions, the light is received by a sensor which generates an output signal corresponding to the amount of light received at each of such wavelengths. A signal processor determines a value corresponding to the amount or relative amount of each measured specie in the exhaust gas, based at least in part on the corresponding output signals from the sensor. The processor also determines the engine's operating condition based at least in part on the output signals corresponding to $H_2O$, $CO_2$ and CO. In particular, the processor determines whether the engine is in normal operating condition, rather than in cold-start or warm-up condition.

3 Claims, 4 Drawing Sheets

EXHAUST EMISSIONS ANALYSIS APPARATUS AND METHOD

INTRODUCTION

This invention is directed to an improved apparatus and method for analysis or testing of exhaust gas emissions from an internal combustion engine, and is especially advantageous for remote testing of exhaust gas emissions from an engine of an on-road motor vehicle, including means for remote determination of the engine's operating condition.

BACKGROUND

Remote analysis or measurement of on-road vehicle emissions is useful in determining and controlling the impact of vehicle emissions on the environment. As used here, remote analysis of on-road vehicle emissions refers to the monitoring, testing or other analysis of exhaust gas from a motor vehicle which is not physically connected to the testing apparatus and, typically, may be moving past the testing apparatus on a public roadway or the like. Studies involving remote testing of on-road vehicle emissions conducted to date having experienced significant inconsistency in test results. Two studies, for example, Stevens et al "*Real World Emissions Variability as Measured by Remote Sensors*" SAE Technical Paper 940582 (1984) and Stedman et al, "*On-Road Remote Sensing of CO and HC Emissions in California,* California Air Resources Board, Final Report AO32-093 (February, 1994), compared the output of two remote sensors measuring the same vehicles only hundreds of feet apart. These studies showed that emission measurements for the same vehicle would occasionally be significantly but unpredictably different as measured by different test devices. These vehicle have been referred to in the literature as "flippers." The flipper phenomenon has not been well understood or explained, but driver variability provides an inadequate explanation of the test differences.

A first aspect of the contribution of the present invention relates to the understanding that test result variability is explainable in large part based on the operating condition of the engine of the motor vehicle. More specifically, test result variability is now understood to be due in large measure to a vehicle being tested at a first site shortly after engine start-up when the engine and exhaust system of the vehicle have not as yet reached normal operating conditions, most particularly normal operating temperatures. The same vehicle subsequently tested at a second site, having warmed on route from the first test site to such second test site, produces substantially different emissions test results.

Accordingly, in order to effectively use remote sensing devices to analyze on-road vehicle emissions, it is now understood to be important to determine whether the vehicle being tested has reached its normal operating condition. That is, apparatus and methods for remote testing of exhaust gas emissions from an internal combustion engine of an on-road motor vehicle should include some way of remotely determining whether the engine of the tested vehicle has reached normal operating condition. Suitable methods to directly measure engine temperature of a passing vehicle would require complicated equipment and would be subject to background influences which may result in insufficient sensitivity and reliability.

It is an object of this invention to provide emissions testing apparatus and methods. It is a particular object of certain embodiments to enable remote testing of exhaust gas emissions, including means for determining whether the engine which is the source of the emissions has reached normal engine operating conditions. It is a further object to provide remote sensing methods which are suitable for use in the field with good reliability. Additional objects of the invention will be understood from the following disclosure and detailed description.

SUMMARY

In accordance with a first aspect, apparatus is provided for testing exhaust gas emissions from an internal combustion engine, including determination of the engine's operating condition. Light is sensed from the exhaust gas emissions, preferably at infrared wavelengths, corresponding to the emission species to be detected or measured, i.e., at wavelengths emitted or absorbed by species. An emissions species here refers to a selected gaseous compound found in the emissions being tested. Infrared light originating at the exhaust plume is received by a sensor and can be analyzed, for example, using Fourier Transform infrared analysis in accordance with known techniques, for wavelengths emitted by the emissions species. Optimally, a light source is employed to emit light of suitable intensity and wavelength toward the exhaust gas emission to be tested. The emitted light should include wavelengths absorbed by the emission species to be detected or measured. It is a particular aspect of the apparatus and method disclosed, that the light be analyzed for wavelengths corresponding to (i.e., emitted or absorbed by) emission species including at least $H_2O$, $CO_2$ and CO. Typically, not all gaseous compounds potentially present in the emissions is tested. Various hydrocarbon compounds may be present, for example, only some or none of which may be tested. As mentioned above, a sensor is provided for receiving light from the exhaust gas emissions. For convenience, such light may be referred to below as emitted light, meaning either it originated at the exhaust gas or originated at a separate light source and was "emitted" by the exhaust gas following its impingement on the emissions. Preferably, impingement involves the emitted light passing through the emissions. In one preferred embodiment, for example, light is emitted from a light source positioned along one side of a road way so as to pass through the emission plume of a passing motor vehicle to a reflector on the opposite side of the roadway. The reflected light passes through the emissions plume a second time (for enhanced test accuracy) before being received at a sensor positioned proximate the light source on the first side of the roadway. For each tested species, the sensor generates an output signal corresponding to an amount value for that species, i.e., to a value related to the absolute or relative amount of that species in the exhaust plume, based on the amount of light received at the wavelength(s) mentioned above corresponding to the emissions species. Preferably, the output signal is a variable voltage signal, such that the voltage corresponds to the amount of received light. Most preferably, a light source is used in the near to mid-infrared wavelength range in which numerous absorption features are available for exhaust gas emissions species. Thus, for example, a so-called glow bar type emitter or other infrared light emitter may be used for non-dispersive infrared analysis techniques, or a tunable diode laser may be used to sequentially emit a series of wavelengths corresponding to the emission species to be tested. Those who are skilled in the art, that is, those who are skilled in this area of technology will recognize that appropriate filter means may be used, particularly if a broad band infrared emitter such as a glow bar type emitter is used, together with either multiple detectors or a single detector having means for modulating the detector frequency to test in turn for $H_2O$, $CO_2$, CO, etc. The output signal from the sensor is received by a signal processor which determines for each of the emission species to be tested an amount value, as mentioned above, based at least in part on the corresponding output signal. It should be recognized in this regard, that reference here to reliance on a single absorption wavelength for testing a given emission species is intended to include various alternative techniques in which multiple features of a species' absorption spectrum are relied upon to determine an amount value for that species. As mentioned above, the amount value may represent an absolute quantity or concentration of the tested species or, more typically, a proportional amount relative one or more other species.

In accordance with a significant aspect of the invention, the engine's operating condition also is determined based at least in part on the output signals corresponding to $H_2O$, $CO_2$ and CO. As mentioned above, emissions testing produces non-representative results for the vehicles operating under cold-start strategies which can dramatically influence emission levels. The cold-start condition occurs for a short period of time and is generally accompanied by emissions not representative of those produced during normal operating conditions. As discussed in more detail below, it is here disclosed to use the aforesaid output signals (e.g., by using the corresponding amount values) for $H_2O$, $CO_2$ and CO to determine whether an engine, and in particular for example, the engine and exhaust system of a passing motor vehicle, are operating under cold-start conditions.

In accordance with another aspect, a method is provided for analysis of exhaust gas emissions, including determination of the engine's operating condition, as discussed above.

It is especially significant and advantageous for improved reliability in remote testing of on-road motor vehicles that the apparatus and method disclosed here for determining engine operating condition (which should be understood to include primarily the temperature of the engine, exhaust system, etc.) is substantially independent of an engine's type, size and fuel management system. Moreover, equipment and systems presently employed for remote emissions testing is readily employed in the present invention, as will be the improvements likely to be developed over time in light sources, sensors and signal processors. These and additional features and advantages of the invention will be better understood from the following detailed description of certain preferred embodiments.

BRIEF DESCRIPTION OF THE DRAWINGS

Preferred embodiments are described below in connection with the following drawings in which.

DETAILED DESCRIPTION OF CERTAIN PREFERRED EMBODIMENTS

Figure 1:
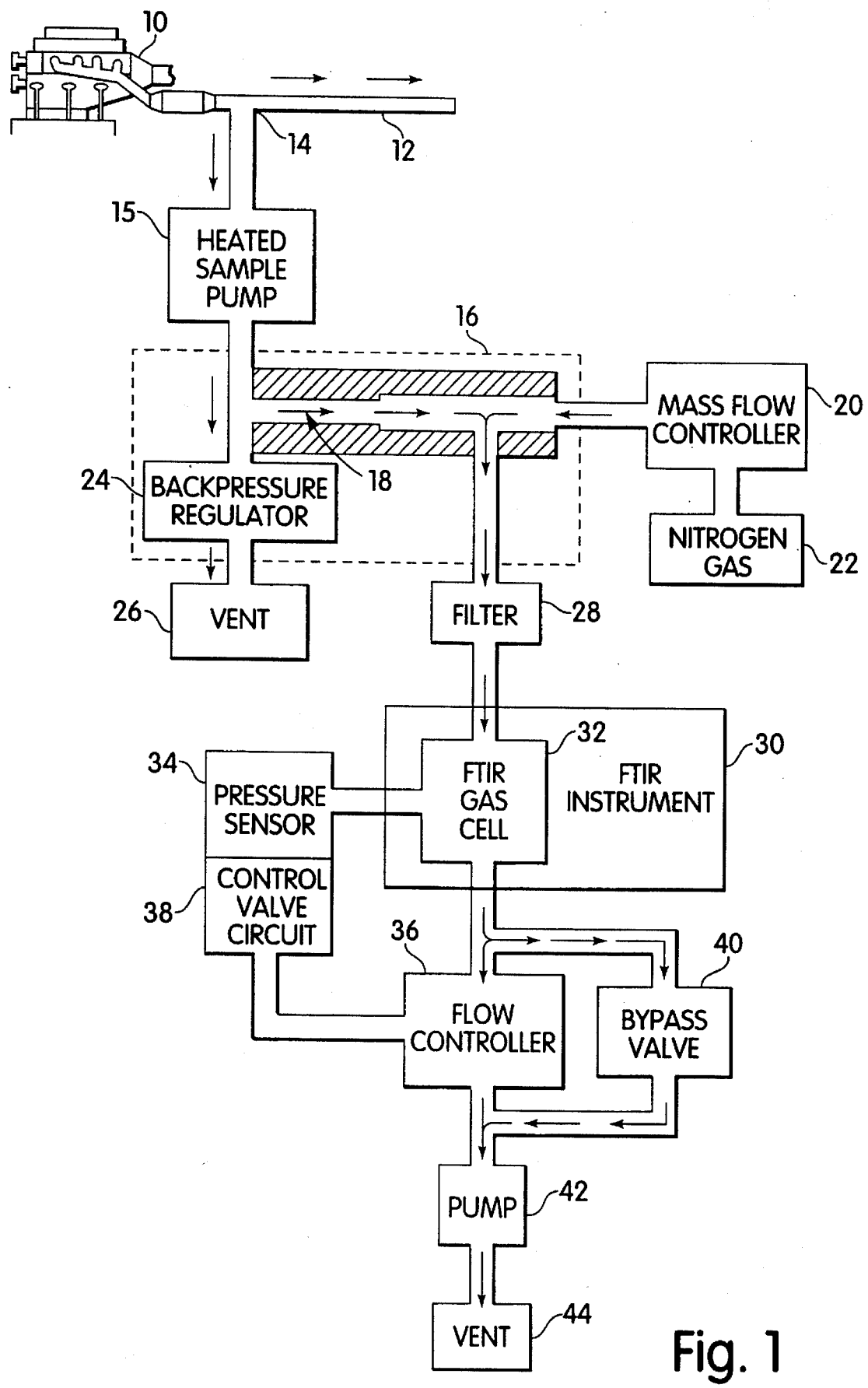
FIG. 1 is a schematic diagram of a method and apparatus for testing exhaust gas emissions from an internal combustion engine and for determining the engine's operating condition, in accordance with a first preferred embodiment.

Under cold-start conditions, modern electronic engine control systems usually implement special interim fuel control strategies which differ from the emissions minimizing strategies used once the engine has reached normal operating conditions, including normal operating temperatures. Thus, in order to effectively use remote sensing devices to measure accurate fleet average vehicle emissions, it is advantageous to ensure that vehicles being tested have reached their normal operating condition. Measurements for environmental testing and control and like purposes should generally not include recently started vehicles operating under cold-start engine control strategies which typically would dramatically influence emissions levels for a short period of time, which could be misinterpreted as fully equilibrated long term emission levels. In addition, irrespective of electronic engine control strategy, three stages occur in sequence following engine start-up, which effect emissions and, in particular, the $H_2O/CO_2$ ratio. First, water condenses in the exhaust system, that is, the exhaust pipe, catalyst, muffler, tailpipe, etc. Until these exhaust components warm sufficiently, the concentration of water exiting the tailpipe is lower than theoretically predicted by the combustion equation. Hence, the $H_2O/CO_2$ ratio in the exhaust emissions is substantially less than stoichiometric combustion would be expected to produce. Second, as the exhaust system components warm, water no longer condenses but, rather, previously condensed water begins to vaporize into the exhaust stream. This operating condition results in the enrichment of water in the exhaust and, consequently, the $H_2O/CO_2$ ratio in the exhaust is substantially higher than would be expected from stoichiometric combustion. Finally, the exhaust system no longer retains or emits condensed water of combustion and the theoretical $H_2O/CO_2$ ratio is achieved for a properly-functioning engine. Thus, for better testing reliability and more reproducible results, remote sensor testing systems and apparatus of the present invention include means for determining whether the tested vehicle has reached normal operating conditions.

Without wishing to be bound by theory, it is generally understood that, to first order approximation, the hydrogen/carbon ratio ("H/C ratio") of the fuel limits the concentration of the hydrogen and carbon containing compounds formed in the vehicle exhaust. Typically, this approximation is little influenced by the combustion of non-fuel sources of hydrogen and carbon, such as lubricating oils, etc. The air/fuel ratio of the combustion process determines the nature of the hydrogen and carbon containing chemical species formed. Under ideal conditions, that is, stoichiometric combustion, the only species formed are carbon dioxide and water. Under less ideal conditions, the species formed typically include, in addition to water and carbon dioxide, carbon monoxide, various hydrocarbons and hydrogen. The general combustion equation for the stoichiometric condition is:

$$CH_nO_m + B\ Air \rightarrow CO_2 + n/2\ H_2O + 0.21(B-B_0)O_2 + 0.78N_2 + 0.01B\ X \qquad (1)$$

where:
n=hydrogen/carbon ratio ("H/C ratio");
m=oxygen/carbon ratio;
B=Moles of air per mole of fuel;
$B_o=[1+n/4-m2]/0.21$; and
X=components in air other than $O_2$ and $N_2$.

Equation (1) above shows that under normal operating stoichiometric conditions, the ratio $H_2O/CO_2$ is substantially constant and is directly related to the H/C ratio of the fuel. Under fuel lean operation conditions, where there is excess air in the exhaust, the above equation becomes:

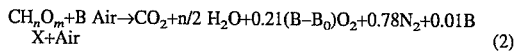
(2)

Equation (2) also shows a constant $H_2O/CO_2$ exhaust gas ratio related only to the H/C ratio of the fuel, since the excess air dilutes both the $H_2O$ and $CO_2$ exhaust species. Accordingly, in both the stoichiometric and lean burn situations, the ratio of the water and carbon dioxide should be substantially a constant, predictable based upon the H/C ratio of the fuel. If the exhaust H/C is less than the target value by an amount which exceeds a pre-selected variance amount, for example, about 0.1, then water vapor is taken to be condensing in the exhaust system. Correspondingly, if it is greater than the target value by more than 0.1 or other preselected variance, then water is being vaporized from the exhaust system and, again, the engine is not yet at normal operating conditions. If the exhaust H/C ratio is within the preselected variance of the target value, then the engine is taken to be at normal operating conditions and other emissions measurements performed in accordance with techniques well understood by those skilled in the art can be performed with improved confidence that the engine is at normal operating conditions and that the measurements are, in that respect, reliable.

It will be understood by those skilled in the art that the exhaust H/C ratio of an engine experiencing warm-up would transition from an excessively low value to an excessively high value, briefly passing through the target value. The time duration during which the $H_2O/CO_2$ ratio of the exhaust would falsely indicate normal engine operating conditions is sufficiently brief (perhaps about 2 seconds out of a 5-minute warm-up process for a typical motor vehicle) as to involve a very small and generally acceptable percentage of vehicles in any emissions-testing program.

By way of example, the H/C ratio of gasoline as presently formulated in the United States is approximately 1.8. Thus, the H/C ratio in the exhaust, will likewise be 1.8, unless cold-start conditions are causing water vapor in the exhaust to be condensed or vaporized in the exhaust system. Since there are two hydrogens in each water molecule, the exhaust $H_2O/CO_2$ ratio at stoichiometry is one-half the fuel H/C ratio and, thus, the target value for gasoline engines in the U.S. is approximately 0.9. The corresponding target value for engine's operating on the methanal-gasoline blend M-85 is 1.7.

The maximum amounts of $H_2O$ and $CO_2$ produced at stoichiometric combustion for gasoline in the U.S. (H/C ratio=1.85) and for the methanol-gasoline blend M-85 (H/C ratio=3.41, O/C ratio=0.72) are given in Table 1 immediately below:

TABLE 1

Maximum Concentrations of Water and Carbon Dioxide Produced at Stoichiometric Combustion

| Compound | Gasoline | Methanol/Gasoline (M-85) |
|---|---|---|
| $CO_2$ | 13.47% | 12.04% |
| $H_2O$ | 12.46% | 20.51% |
| $H_2O/CO_2$ | 0.925 | 1.70 |

Thus, the engine operating condition (cold, warming or normal) can be reliably inferred via real-time monitoring of the H/C ratio in the exhaust plume of a vehicle. Further, this parameter is substantially unaffected by the type of engine, the type of fuel management system (carbolated or fuel-injected) and the air/fuel ratio.

As indicated above, it is a significant, novel aspect of the method and apparatus disclosed here that the engine operating condition is determined based on the relative concentrations of $H_2O$, $CO_2$ and CO in the exhaust gas emissions. Without wishing to be bound by theory, the following explanation relates to the significant point that the exhaust H/C ratio (which, as just discussed, is a reliable indicator of whether an engine is at normal operating conditions) can be reliably inferred with sufficient accuracy from the measurement of the three exhaust components $H_2O$, $CO_2$ and CO.

Modern electronic engine management strategies, as indicated above, typically implement fuel enrichment under cold-start conditions and, accordingly, are accompanied by the production of rich combustion by-products, such as carbon monoxide, various hydrocarbons and hydrogen. Typically, carbon monoxide can be a significant fraction of the exhaust from either a cold start condition or from a poorly operating engine. In order to accurately infer the exhaust H/C ratio from exhaust gas analysis, carbon monoxide must be accounted for in the measurements. The generally equation which relates H/C ratio to exhaust components is:

$$\frac{H}{C} \text{ ratio} = \frac{H_2O + H_2}{CO_2 + CO + HC} \quad (3)$$

The "water gas shift reaction" predicts the hydrogen concentration in gasoline engine exhaust to be one-third the carbon monoxide concentration. Under poor operating conditions, the hydrogen concentration in the exhaust may be significant, but this would occur with correspondingly high CO emissions. Hydrocarbon emissions represent a small fraction of the total carbon in engine exhaust, typically being less than 0.5%. Accordingly, it can be deleted from Equation (3) without significant impact on the reliability or accuracy of test results. Therefore, Equation (3) becomes:

$$\frac{H}{C} \text{ ratio} = \frac{H_2O + H_2}{CO_2 + CO} \quad (4)$$

Rather than measuring absolute quantities of these emission species in an exhaust plume of a passing vehicle, the necessary values can be obtained by measuring ratioed values which substantially eliminate the effects of exhaust mixing, exhaust plume disbursion, etc. If the water gas shift relationship is introduced and the components measured are ratioed to the $CO_2$ output signal of the sensor, Equation (4) becomes:

$$\frac{H}{C} \text{ ratio} = \frac{(H_2O/CO_2) + (CO/CO_2)/3}{1 + (C/CO_2)} \quad (5)$$

From Equation (5) it can be seen that the exhaust H/C ratio can be accurately inferred from the measurements of three exhaust components, $H_2O$, $CO_2$ and CO. As discussed above, the exhaust H/C ratio is a reliable determinant of whether or not an engine is at normal operating conditions.

In general, it is presently understood to be an acceptable assumption that if the $H_2O/CO_2$ ratio is greater than about 2.3, the vehicle is burning methanal-gasoline blend M-85 rather than gasoline. Thus, combustion fuel type also is testable in accordance with this disclosure. If vehicles burning M-85 are to be included in an emissions test program, the processing means can be programmed in accordance with techniques well-known to those skilled in the art not to exclude vehicles whose inferred H/C ratio falls within either of two target ranges, one centered on the target value for gasoline and the other centered on the target value for M-85.

Example I

The method and apparatus schematically illustrated in FIG. 1 was used for testing exhaust gas emissions from a 1993 model year Aerostar minivan equipped with a 3.0 L six cylinder engine. The vehicle was driven using the Bag 1 of the Urban Dynamometer Driving Schedule (UDDS). The exhaust was analyzed for $H_2O$, $CO_2$ and CO by Fourier Transform Infrared Analysis (FTIR) as described in C. A. Gierczak et al, *On-Board Vehicle Emissions Measurement Program, Final Report, CRC Contract VE*-11-1 (April 1994), which is incorporated herein by reference. As seen in FIG. 1, a sample stream of exhaust gas from the engine 10 was taken from the exhaust conduit 12 at a point 14 approximately 1 meter downstream of the engine by means of a heated sample pump 15. The exhaust was passed through a heated zone 16 having a flow restriction 18. This sampling point was well upstream of most of the exhaust system components, such that the exhaust gas would be representative of uncondensed engine exhaust. The flow of the exhaust sample was controlled by mass flow controller 20, having a source of nitrogen gas 22 and by back pressure regulator 24 communicating with a vent 26 to atmosphere. The exhaust sample passed through filter 28 to a standard FTIR instrument 30 comprising an FTIR gas cell 32 exposed to a pressure sensor 34 adapted to actuate flow controller 36 by means of control valve circuit 38. Sample gas exiting the FTIR gas cell 32 proceeds either through flow controller 36 or optional bypass valve 40 through pump 42 and vent 44 to atmosphere.

Figure 3:
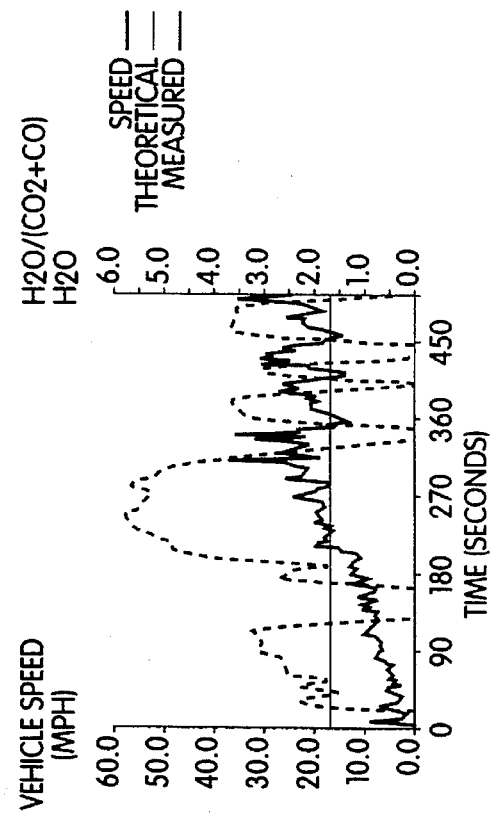
FIG. 3 is a graph showing test results obtained using the apparatus and method of FIG. 1.

The graph of FIG. 3 shows the inferred exhaust H/C ratio determined by equation 5 above, based on the measurement of $H_2O$, $CO_2$ and CO. FIG. 3 also shows vehicle speed and the theoretical exhaust H/C ratio of about 0.92. The time line covers the first 505 seconds of the UDDS (i.e., Bag 1). The graphical results show that the inferred H/C ratio exceeds the theoretical value within fifty seconds after the vehicle was started, and then stabilizes at approximately the theoretical value for the remainder of the test period. This is consistent with the exhaust sample being taken very near the exhaust manifold of the engine, such that the hot engine exhaust quickly heats the exhaust pipe, preventing water condensation and quickly achieving equilibrium. Once the exhaust temperature stabilizes, the variation in the inferred H/C ratio is shown to be minimal (0.96±0.04). Thus, the inferred H/C ratio is shown to be reliably a nearly constant value once water condensation and water vaporization cease at normal engine operating conditions.

Example II

Figure 2:
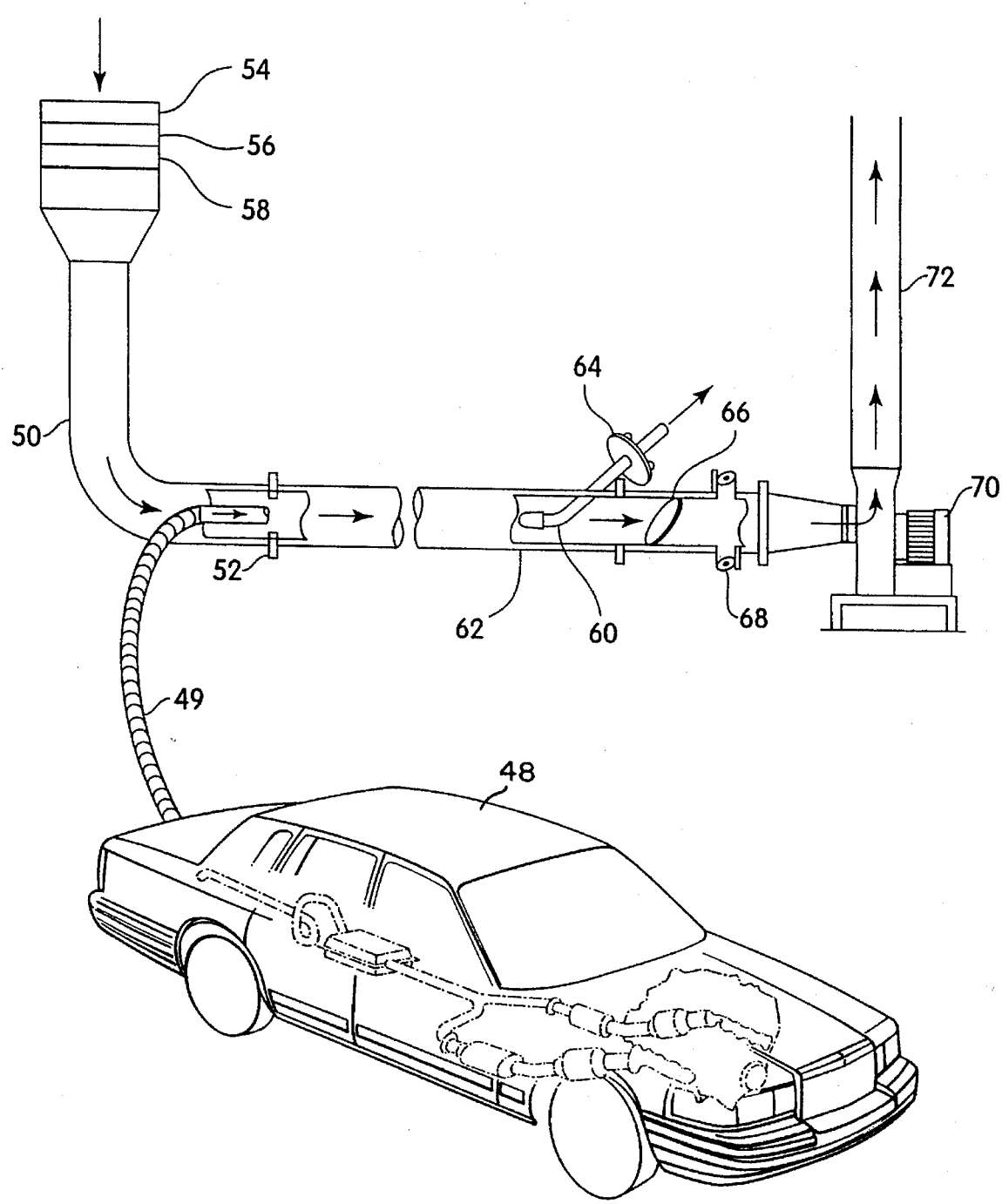
FIG. 2 is a schematic illustration of apparatus in accordance with a second embodiment.

A 1991 model year Taurus vehicle equipped with a 3.0 L six cylinder engine fueled with M-85, was driven over the entire UDDS. Exhaust from the vehicle was transferred to a dilution tube as illustrated in FIG. 2. Dilution of the exhaust prevented condensation and the diluted exhaust was analyzed for $H_2O$, $CO_2$ and CO by FTIR. As seen in FIG. 2, exhaust from vehicle 48 entered a dilution tube 50 immediately upstream of a mixing baffle 52. Dilution tube 50 was equipped with a filter 54, air conditioner/dehumidifier 56, and heater 58 for treatment of incoming diluent air. Downstream of the mixing baffle 52, a sampling probe 60 proximate a thermocouple 62 directed diluted exhaust through filter 64 to an FTIR instrument substantially as described in Example 1. Flow within dilution tube 50 was controlled by throttle valve 66, bypass valve 68, and fan 70 communicating with vent stack 72.

Figure 4:
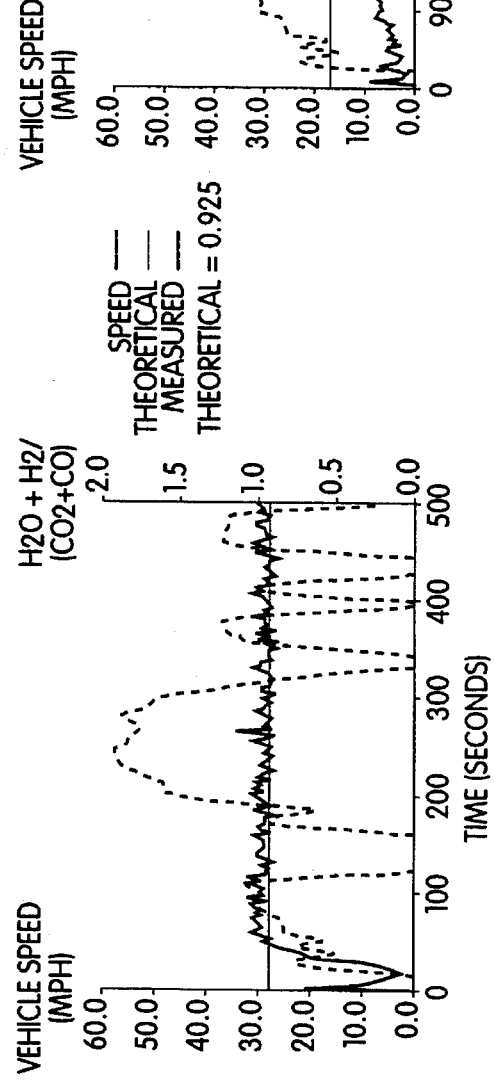
FIGS. 4-6 are graphs showing test results obtained using the apparatus of FIG. 2.
Figure 6:
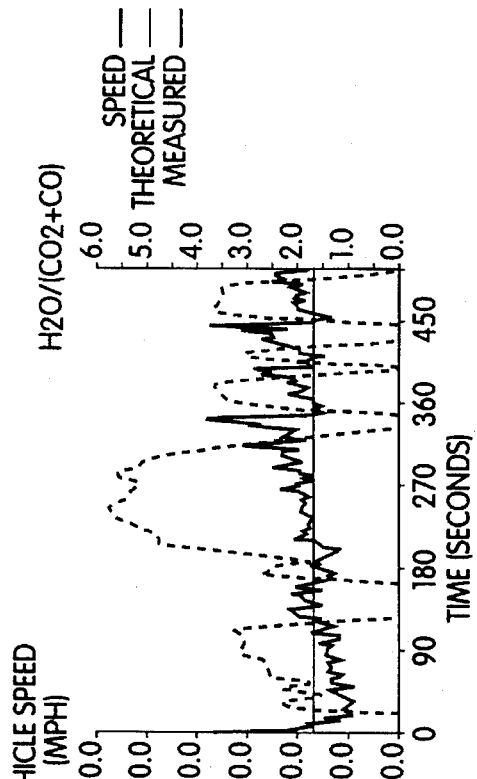
Figure 5:
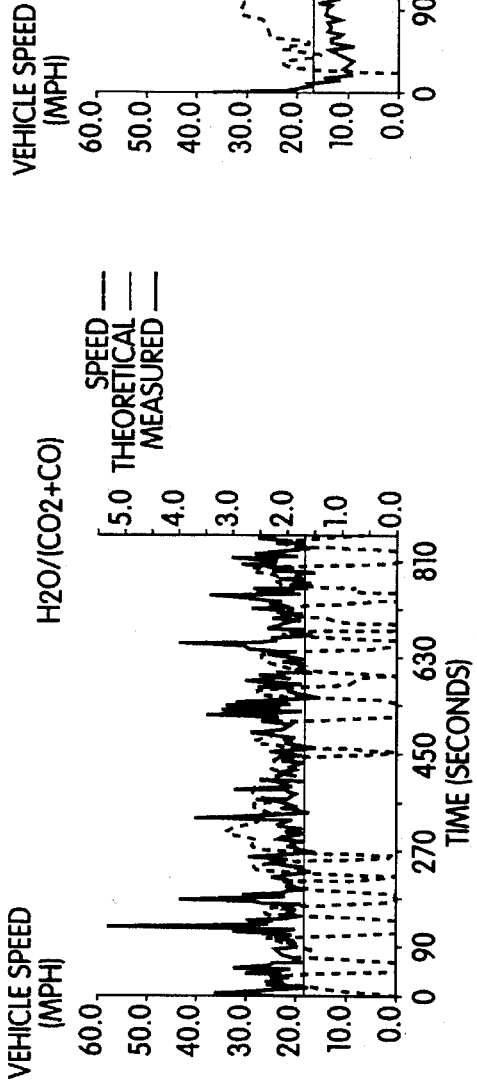

Contribution of $H_2$ to the inferred H/C ratio was neglected, causing less than one percent error in the inferred exhaust H/C ratio based on measured CO levels. FIG. 4 shows vehicle speed and the theoretical exhaust H/C ratio of 1.7 for M-85. M-85 combustion produces higher concentrations of water in the exhaust gas by a factor of approximately 2. (See table 1 above). The exhaust H/C ratio is well below the theoretical value initially, and then rises above the theoretical H/C ratio value. This corresponds to water loss from the exhaust gas due to condensation within the exhaust system of the vehicle occurring for approximately 210 seconds, followed by vaporization of the condensed water from the exhaust system for the next 140 seconds. The H/C ratio then tends to vacillate above and below the theoretical value, with high values corresponding to low speed or idle conditions, that is, conditions of high. sample dilution. Highly diluted samples are relatively drier, and condensed water is more readily evaporated by the drier airstream than in a less diluted sample. Viewed in conjunction with the expected constant inferred exhaust H/C ratio value from FIG. 3, some water is believed to have been condensed in the unheated transfer line 49 (see FIG. 2) from the vehicle to the dilution tube. Corresponding results are seen in FIG. 5 for Bag 2 of the UDDS. In remote testing of on-road vehicles, no such loss due to condensation would occur in exhaust beyond the tailpipe of the vehicle. Thus, one would obtain the constant exhaust H/C ratio values corresponding more nearly to the results illustrated in FIG. 3. The graph of FIG. 6 illustrates the last 505 seconds of the UDDS (Bag 3). This portion of the UDDS follows the results shown in FIGS. 4 and 5 with a subsequent ten minute soak, during which the engine is turned off and allowed to cool. The test results illustrated in FIG. 6 indicate that condensed water in the exhaust system is evaporated during the initial fifteen seconds following engine restart, resulting in a high H/C ratio value. Thereafter, a low H/C ratio value is seen as water is condensed in the exhaust system. The engine operating condition stabilizes at approximately 350 seconds after engine restart.

Figure 7:
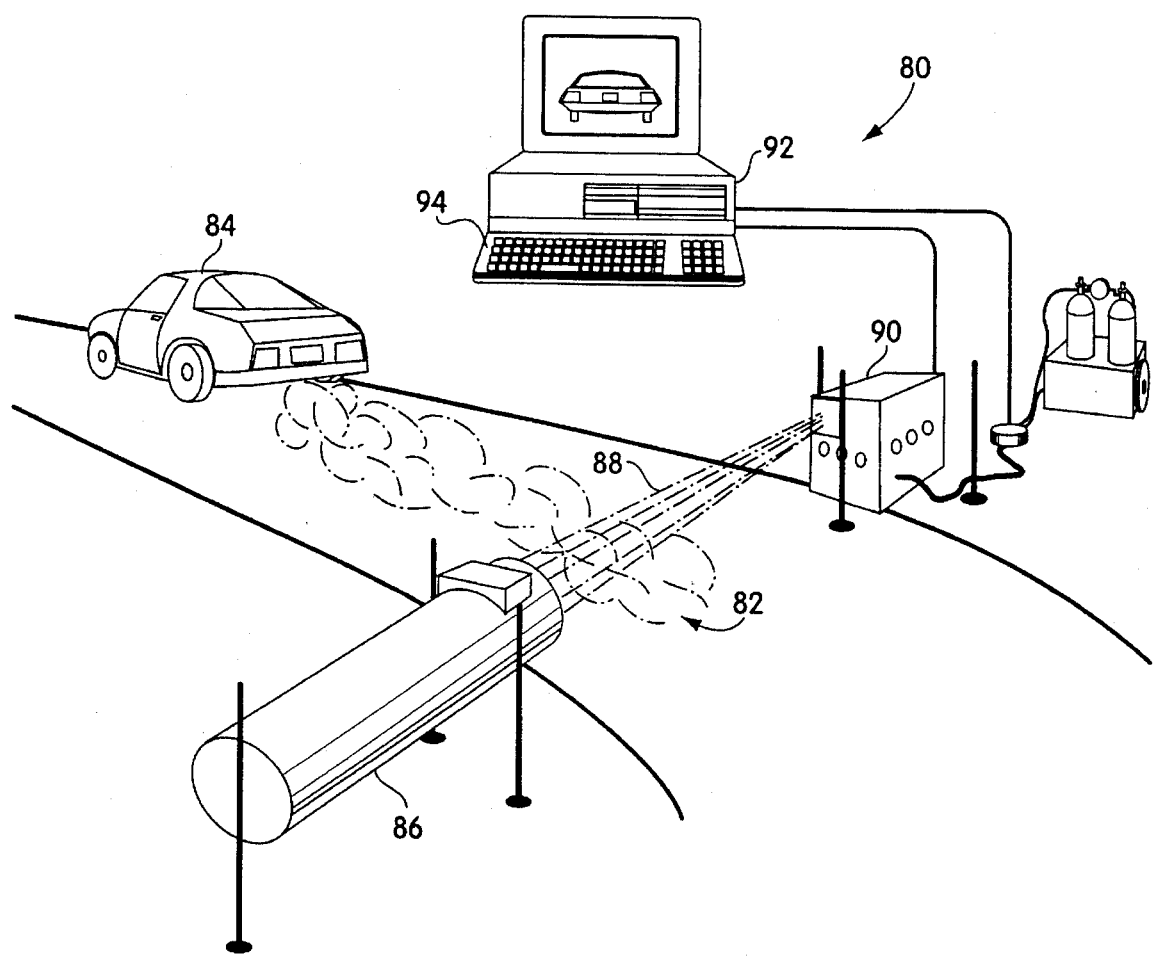
FIG. 7 is a schematic illustration of a preferred embodiment of an emissions testing system for remote testing of exhaust gas emissions from the internal combustion engine of on-road motor vehicles, and for remote determination of the operating condition of the motor vehicle engines.

An emissions testing system 80 in accordance with a preferred embodiment is schematically illustrated in FIG. 7, for remote testing of exhaust gas emissions 82 from an internal combustion engine of an on-road motor vehicle 84 and for remote determination of the engine's operating condition. A tunable diode laser 86 is provided for emitting near to mid-infrared light 88 through the vehicle emissions, at a sequence of wavelengths absorbed by corresponding emission species to be measured, including at least $H_2O$, $CO_2$ and CO. Sensor means 90 are provided for receiving the light after it has passed through the vehicle emissions. The sensor means comprises a detector adapted to generate an output signal for each of the emission species at a voltage proportional to the amount of light received at each such wavelength. Microprocessor 92 is provided for receiving such output signals from the detector 90. The microprocessor determines at least a relative amount value for each of the emission species, based at least in part on the corresponding output signal for that species. The microprocessor further determines a value corresponding to inferred exhaust H/C ratio in accordance with equation 5 above. Such inferred H/C ratio value is then employed by the microprocessor for determining the engine's operating condition. Specifically, such value is compared by the microprocessor to a preselected value range preferably stored in ROM memory 94 associated with the microprocessor. Such preselected value range, as is discussed above, corresponds to a normal engine operating condition.

It will be apparent to those skilled in the art from the foregoing disclosure, that various modifications, additions and the like can be made to the preferred embodiments discussed above of this novel apparatus and method for testing exhaust gas emissions, without departing from the true scope and spirit of this invention.

I claim:

1. An apparatus for testing of exhaust gas emissions from an internal combustion engine and for determination of an operating condition of the engine, comprising:

sensor means for receiving light from the exhaust gas emissions at wavelengths corresponding to emission species to be detected, including at least $H_2O$, $CO_2$ and CO, and for generating an output signal corresponding to an amount of light received at each of said wavelengths;

signal processor means for receiving the output signals and determining an amount value for each of said emission species based at least in part on the corresponding output signal, and for determining the operating condition based at least in part on the output signals corresponding to $H_2O$, $CO_2$ and CO; and emitter means for emitting light toward the exhaust gas emissions, having wavelengths absorbed by emission species to be detected, including at least $H_2O$, $CO_2$ and CO;

wherein the signal processor means comprises a microprocessor for determining a value corresponding to exhaust H/C ratio equal to:

$$\frac{H}{C} \text{ ratio} = \frac{H_2O}{CO_2} + \frac{\frac{CO/CO_2}{3}}{1 + (CO/CO_2)}$$

where:

$H_2O$ is the amount value determined by the signal processor means for $H_2O$,

$CO_2$ is the amount value determined by the signal processor means for $CO_2$, and

CO is the amount value determined by the signal processor means for CO, and for determining the operating condition at least in part by comparing the exhaust H/C ratio value to a preselected value range corresponding to normal engine operating conditions, and for manifesting whether the exhaust H/C ratio is within said preselected value range.

2. The apparatus for testing of exhaust gas emissions from an internal combustion engine, and for determination of an operating condition of the engine in accordance with claim 1, wherein the preselected value range is stored in ROM memory of the microprocessor.

3. An emissions testing system for remote testing of exhaust gas emissions from an internal combustion engine of an on-road motor vehicle and for remote determination of an operating condition of the engine, comprising:

a tunable diode laser for emitting near to mid-infrared light through the vehicle emissions, at a sequence of wavelengths absorbed by corresponding emissions species to be measured, including at least $H_2O$, $CO_2$ and CO;

sensor means for receiving the light after passing through the vehicle emissions at least once, comprising a detector means for generating an output signal for each of said emission species at a voltage proportional to an amount received of said light at the corresponding wavelength; and microprocessor means for receiving output signals from the sensor means and determining at least a relative amount value for each of said emission species, based at least in part on the output signal for that species, and for determining a value corresponding to exhaust H/C ratio equal to:

$$\frac{H}{C} \text{ ratio} = \frac{H_2O}{CO_2} + \frac{\frac{CO/CO_2}{3}}{1 + (CO/CO_2)}$$

where:

$H_2O$ is the amount value determined by the signal process means for $H_2O$,

$CO_2$ is the amount value determined by the signal processor means for $CO_2$, and

CO is the amount value determined by the signal processor means for CO, and for determining the operating condition at least in part by comparing the exhaust H/C ratio value to a preselected value range stored in ROM memory of the microprocessor means corresponding to normal engine operating conditions.

* * * * *

UNITED STATES PATENT AND TRADEMARK OFFICE
CERTIFICATE OF CORRECTION

PATENT NO. : 5,621,166
DATED : April 15, 1997
INVENTOR(S) : James W. Butler

It is certified that error appears in the above-identified patent and that said Letters Patent is hereby corrected as shown below:

Column 6, Equation (5) should appear as follows:

$$\frac{H}{C} \text{ ratio} = \frac{(H_2O/CO_2) + (CO/CO_2)/3}{1 + (CO/CO_2)}$$

Claim 1, at line 23, (Col. 9, lines 28-30), the equation should appear as follows:

$$\frac{H}{C} \text{ ratio} = \frac{(H_2O/CO_2) + (CO/CO_2)/3}{1 + (CO/CO_2)}$$

Claim 3, at line 22, (Col. 10, lines 28-31), the equation should appear as follows:

$$\frac{H}{C} \text{ ratio} = \frac{(H_2O/CO_2) + (CO/CO_2)/3}{1 + (CO/CO_2)}$$

Signed and Sealed this

Fifteenth Day of September, 1998

*Attest:*

BRUCE LEHMAN

*Attesting Officer*            *Commissioner of Patents and Trademarks*